US006211378B1

(12) United States Patent
Babiarz et al.

(10) Patent No.: US 6,211,378 B1
(45) Date of Patent: Apr. 3, 2001

(54) PROCESS FOR THE SYNTHESIS OF 4-SUBSTITUTED N-[(ALK-2-EN-1-YL)OXY]- AND N-ARALKYLOXY-2,2,6,6-TETRAALKYLPIPERIDINES

(75) Inventors: Joseph E. Babiarz, Amawalk, NY (US); Stephen D. Pastor, Danbury; Glen T. Cunkle, Stamford, both of CT (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/315,705

(22) Filed: May 20, 1999

Related U.S. Application Data

(60) Provisional application No. 60/103,951, filed on Oct. 13, 1998.

(51) Int. Cl.[7] .................................................. C07D 211/36
(52) U.S. Cl. ............................................................. 546/242
(58) Field of Search ............................................... 546/242

(56) References Cited

U.S. PATENT DOCUMENTS

| | | | |
|---|---|---|---|
| 5,204,473 | 4/1993 | Winter et al. | 546/188 |
| 5,416,215 | 5/1995 | Büschken et al. | 546/184 |
| 5,629,426 | 5/1997 | Pastor et al. | 546/216 |
| 5,654,434 | 8/1997 | Pastor et al. | 546/242 |
| 5,777,126 | 7/1998 | Pastor et al. | 546/244 |

OTHER PUBLICATIONS

E. G. Rozantsev et al., Synthesis, 1971, 190.
I. Q. Li et al., Macromolecules 1996, 29,8554.
T. J. Connolly et al., Tetrahedron Letters, 1996, 37,4919.
I. A. Opeida, et al., Kinetics and Catalysts, 1995, (36),441.
Linda J. Johnston, et al., J. Org. Chem., vol. 51, No. 14, 1986, 2807.
Davenport, et al., Macromolecules, vol. 30, No. 7, 1997, 1930.
Terrence J. Connolly, et al., Tetrahedron Letters, vol. 38, No. 7, pp. 1133–1136, 1997.

*Primary Examiner*—John Kight
*Assistant Examiner*—Raymond Covington
(74) *Attorney, Agent, or Firm*—Luther A. R. Hall

(57) ABSTRACT

An environmentally friendly process for the preparation of the 4-functionalized N—OR derivatives of 2,2,6,6-tetraalkylpiperidines involves the hydrogen peroxide of the corresponding N—H compound to form the corresponding N-oxyl derivative, reacting two equivalents of the N-oxyl compound with one equivalent of a compound having an allylic hydrogen, a benzylic hydrogen or an activated methine hydrogen to form one equivalent of the corresponding N—OH compound and one equivalent of the corresponding N—OR compound, and recycling the N—OH compound back to the corresponding N-oxyl compound using hydrogen peroxide or air.

28 Claims, No Drawings

PROCESS FOR THE SYNTHESIS OF 4-SUBSTITUTED N-[(ALK-2-EN-1-YL)OXY]- AND N-ARALKYLOXY-2,2,6,6-TETRAALKYLPIPERIDINES

This application claims the benefit under 35 USC 119(e) of U.S. Provisional Application Ser. No. 60/103,951, filed Oct. 13, 1998.

The instant process pertains to an environmentally friendly process for making 4-functionalized N—OR derivatives of 2,2,6,6-tetraalkylpiperidines.

BACKGROUND OF THE INVENTION

The hydrogen peroxide oxidation of 2,2,6,6-tetramethylpiperidines with hydrogen peroxide alone, or with carbonate catalyst, of with divalent metal catalyst is known. U.S. Pat. Nos. 5,654,434 and 5,777,126 describe the oxidation using hydrogen peroxide alone. U.S. Pat. No. 5,629,426 discloses the use of carbonate catalyzed hydrogen peroxide oxidations. U.S. Pat. No. 5,416,215 describes the use of divalent metal catalysts for the hydrogen peroxide oxidation reaction.

E. G. Rozantsev et al., Synthesis, 1971, 190 disclose the use of tungstate catalyst for the hydrogen peroxide oxidation of 2,2,6,6-tetramethylpiperidines.

U.S. Pat. No. 5,204,473 describes the use of tert-butyl hydroperoxide for the oxidation of 2,2,6,6-tetramethylpiperidines to the corresponding N-oxyl compounds. I. Q. Li et al., Macromolecules 1996, 29, 8554 and T. J. Connolly et al., Tetrahedron Letters, 1996, 37, 4919 describe the use of di-tert-butyl peroxide for the same purpose.

G. G. Barclay et al., Macromolecules, 1997, (30), 1929 describe the formation of a diadduct of a nitroxyl with an activated double bond (styrene).

L. J. Johnson et al., J. of Organic Chem., 1986, (51), 2806 describe the photochemical hydrogen atom abstraction by nitroxyls followed by N—OR formation.

T. J. Connolly et al., Tetrahedron Letters, 1997, (38), 1133 disclose the thermal abstraction of benzylic hydrogen atoms followed by N—OR formation.

I. A. Opeida et al., Kinetics and Catalysts, 1995, (36), 441 (translation from Russian) also describe the thermal abstraction of benzylic hydrogen atoms.

The instant process differs significantly from each of these prior art references and provides the use of environmentally friendly hydrogen peroxide with water as an oxidation by-product. The formation of 4-functionalized N—OR derivatives is obtained without the use of organic peroxides and hydroperoxides.

DETAILED DISCLOSURE

The instant process involves two steps for the preparation of a selected N—OR derivative of the 2,2,6,6-tetraalkylpiperidines with a third step involving the recycling of the N—OH obtained concomitantly with the desired N—OR compound back to the corresponding N-oxyl starting material for the second step.

The overall process is outlined below:

Step 1 (preparing an N-oxyl compound by oxidation with hydrogen peroxide)

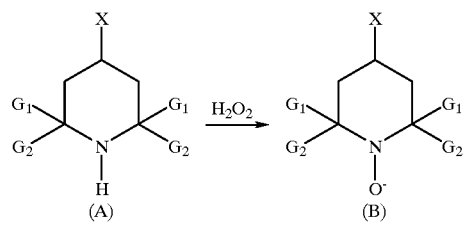

Step 2 (reacting two equivalents of N-oxyl with one allylic, benzylic or activated methine compound (R—H) to form one equivalent of N—OH and one equivalent of N—OR compound)

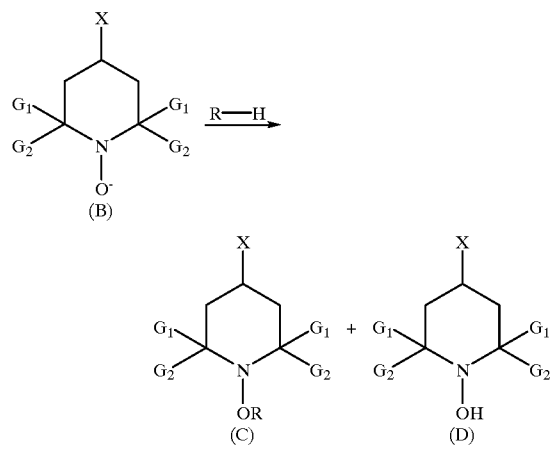

Step 3 (recycling the N—OH compound formed in Step 2 back to the N-oxyl compound needed as intermediate for Step 2)

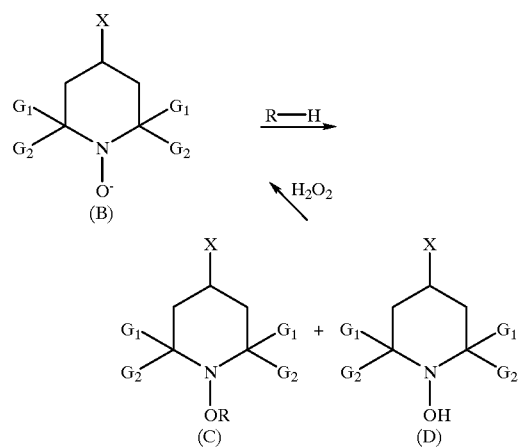

In the formulas A, B, C and D, $G_1$ and $G_2$ are independently alkyl of 1 to 4 carbon atoms, preferably methyl, or $G_1$ and $G_2$ together are pentamethylene;

X is hydrogen, hydroxyl, oxo, —NH—CO—E, —O—CO—E or —NH—CO—NH—E, where E is alkyl of 1 to 18 carbon atoms, said alkyl substituted by hydroxyl or E is aryl of 6 to 10 carbon atoms; and R is as defined below.

In Step 2, the R—H compound is an allylic, benzylic or activated methine compound where the H-atom is highly vulnerable to being extracted by the N-oxyl radical so that the two equivalents of N-oxyl compound essentially react with one equivalent of R—H compound to undergo a disproportionation reaction give one equivalent of N—OR and one equivalent of N—OH. For environmental and economic concerns, it is most expedient to recycle the N—OH compound prepared in Step 3 back to the starting N-oxyl intermediate needed in Step 2.

Preferably, in the compounds of R—H which are allylic in nature, R is an alkenyl of 3 to 20 carbon atoms such as cyclohexene, 1,5-cyclooctadiene, cyclooctene, 1-octene, allylbenzene, α-methylstyrene or β-methylstyrene (1-phenyl-1-propene), and in the compounds of R—H which are benzylic, R—H is a compound of formula Y—CH—Z where Y and Z are independently, hydrogen, alkyl of 1 to 18 carbon atoms, aryl of 6 to 10 carbon atoms or said aryl substituted by one to four alkyl groups of 1 to 4 carbon atoms, provided that at least one of Y and Z is aryl and where is Y is aryl, then Z can be part of a fused ring system having methylene groups such as 1,2,3,4-tetrahydronaphthalene, toluene, o-xylene, m-xylene, p-xylene, diphenylmethane, ethylbenzene, mesitylene or durene.

Most preferably, in Step 2, the compound R—H is cyclohexene, 1,5-cyclooctadiene, cyclooctene, 1-octene, α-methylstyrene, β-methylstyrene, toluene, m-xylene, p-xylene, diphenylmethane or ethylbenzene.

Most preferably, in Step 2, the oxyl compound of formula B is 1-oxyl4-hydroxy-2,2,6,6-tetramethylpiperidine, 1-oxyl-4-acetamido-2,2,6,6-tetramethylpiperidine, 1-oxyl-4-oxo-2,2,6,6-tetramethylpiperidine or 1-oxyl-4-benzoyloxy-2,2,6,6-tetramethylpiperidine.

The instant invention also pertains to the independent process of Step 2 and to the independent process comprising Step 2 and Step 3 together.

Preferably, in Step 1 and in Step 3, the concentration of aqueous hydrogen peroxide is 30% by weight or higher. Aqueous hydrogen peroxide of 30%, 50% or 70% by weight are effective.

Step 1 and Step 3 can be carried out where the hydrogen peroxide oxidation as taught by U.S. Pat. Nos. 5,654,434 and 5,777,126 without catalyst; or as taught by U.S. Pat. No. 5,629,426 using a carbonate catalyst The hydrogen peroxide oxidation of Step 1 and Step 3 can also be carried out in the presence of a tungstate catalyst or divalent metal salts.

Step 2 can be carried out in the absence of solvent or in the presence of an inert solvent such a chlorobenzene.

Step 2 can be carried out at a temperature of 50 to 140° C. at atmospheric pressure or at 50 to 140° C. in a pressure vessel.

The following examples are meant for illustrative purposes only and are not to be construed to limit the instant invention in any manner whatsoever.

EXAMPLE 1

1-(Cyclohex-2-en-1-yl)oxy-4-hydroxy-2,2,6,6-tetramethylpiperidine

A mixture of 17.05 g (0.10 mol) of 1-oxyl-4-hydroxy-2,2,6,6-tetramethylpiperidine and 100 mL (0.99 mol) of cyclohexene under a nitrogen atmosphere is heated at 70° C. for 72 hours. The reaction mixture is filtered to remove 1,4-dihydroxy-2,2,6,6-tetramethylpiperidine and the filtrate is washed with 5 w/v % ascorbic acid (2×50 mL) and distilled water (2×50 mL). The organic phase is dried over anhydrous sodium sulfate and the volatiles are removed in vacuo. The residue is recrystallized from acetonitrile to give 4.44 g (36% yield) of a white solid melting at 65–66.5° C.

$^1$Hnmr (CDCL$_3$)(499.8493 MHz) δ 1.16 (s, 3H), 1.17 (s, 3H), 1.22 (s, 3H), 1.24 (s, 3H), 1.49 (dd, 2H), 1.50–2.10 (overlapping multiplets, 6H), 1.82 (dd, 2H), 3.97 (tt, 1H), 4.25 (m, 1H), 5.81 (ddt, 1H).

Analysis:
  Calc'd for C$_{15}$H$_{27}$NO$_2$: C, 71.10; H, 10.74; N, 5.53.
  Found: C, 71.05; H, 10.59; N, 5.43.

EXAMPLE 2

1-(3-Methylbenzyl)oxy-4-hydroxy-2,2,6,6-tetramethylpiperidine

A mixture of 8.60 g (0.05 mol) of 1-oxyl-4-hydroxy-2,2,6,6-tetramethylpiperidine and 106.17 g (1.0 mol) of m-xylene under a nitrogen atmosphere is heated at 135–136° C. for 69 hours. The reaction mixture is filtered to remove 1,4-dihydroxy-2,2,6,6-tetramethylpiperidine, and the filtrate is washed with 10 w/v % ascorbic acid (3×33 mL) and distilled water (2×50 mL). The organic phase is dried over anhydrous sodium sulfate and the volatiles are removed in vacuo. The residue is recrystallized from heptane to give 3.50 g (51% yield) of a white solid melting at 66–67° C.

IR (1% solution in methylene chloride) v 3600 cm$^{-1}$ (OH).

$^1$Hnmr (CDCL$_3$)(499.8493 MHz) δ 1.21 (s, 6H), 1.31 (s, 6H), 1.52 (dd, 2H), 1.84 (dd, 2H), 2.37 (s, 3H), 3.99 (tt, 1H), 4.79 (s, 2H), 7.11 (d, 1H), 7.16 (d, 1H), 7.24 (t,1H).

Analysis:
  Calc'd for C$_{17}$H$_{27}$NO$_2$: C, 73.61; H, 9.81; N, 5.05.
  Found: C, 73.56; H, 9.70; N, 4.95.

EXAMPLE 3

1-(4-Methylbenzyl)oxy-4-hydroxy-2,2,6,6-tetramethylpiperidine

A mixture of 8.60 g (0.05 mol) of 1-oxyl-4-hydroxy-2,2,6,6-tetramethylpiperidine and 106.17 g (1.0 mol) of p-xylene under a nitrogen atmosphere is heated at reflux for 48 hours. The reaction mixture is filtered to remove 1,4-dihydroxy-2,2,6,6-tetramethylpiperidine, and the filtrate is washed with 10 w/v % ascorbic acid (1×50 mL) and distilled water (2×50 mL). The organic phase is dried over anhydrous sodium sulfate and the volatiles are removed in vacuo. The residue is recrystallized from heptane to give 4.00 g (59% yield) of a white solid melting at 92.5–93° C.

IR (1% solution in methylene chloride) v 3600 cm$^{-1}$ (OH).

$^1$Hnmr (CDCL$_3$)(499.8493 MHz) δ 1.20 (s, 6H), 1.31 (s, 6H), 1.53 (dd, 2H), 1.85 (dd, 2H), 2.36 (s, 3H), 3.99 (tt, 1H), 4.78 (s, 2H), 7.17 (d, 2H), 7.26 (d, 2H).

Analysis:
  Calc'd for C$_{17}$H$_{27}$NO$_2$: C, 73.61; H, 9.81; N, 5.05.
  Found: C, 73.69; H, 9.58; N, 5.02.

EXAMPLE 4

1-(3-Methylbenzyl)oxy-2,2,6,6-tetramethylpiperidin-4-yl Benzoate

A mixture of 13.77 g (0.05 mol) of 1-oxyl-4-benzoyloxy-2,2,6,6-tetramethylpiperidine and 106.17 g (1.0 mol) of m-xylene under a nitrogen atmosphere is heated at reflux for 50 hours. The reaction mixture is filtered to remove the hydroxylamine, and the filtrate is washed with 10 w/v % ascorbic acid (1×50 mL) and distilled water (2×50 mL). The organic phase is dried over anhydrous sodium sulfate and the volatiles are removed in vacuo. The residue is recrystallized from isopropyl alcohol to give 5.62 g (59% yield) of a white solid melting at 64–65° C.

$^1$Hnmr (CDCL$_3$)(499.8493 MHz) δ 1.32 (s, 6H), 1.35 (s, 6H), 1.78 (dd, 2H), 2.02 (dd, 2H), 2.38 (s, 3H), 4.83 (s, 2H), 5.32 (tt, 1H), 7.12 (d, 1H), 7.18 (d, 1H), 7.19 (d, 1H), 7.26 (d 1H), 7.45 (t, 2H), 7.57 (t, 1H), 8.04 (d, 1H).

Analysis:
Calc'd for C$_{24}$H$_{31}$NO$_3$: C, 75.54; H, 8.20; N, 3.67.
Found: C, 74.97; H, 8.12; N, 4.01.

EXAMPLE 5

1-(3-Methylbenzyl)oxy-4-acetamido-2,2,6,6-tetramethylpiperidine

A mixture of 10.67 g (0.05 mol) of 1-oxyl-4-acetamido-2,2,6,6-tetramethylpiperidine and 106.17 g (1.0 mol) of m-xylene under a nitrogen atmosphere is heated at 133° C. for 67 hours. The reaction mixture is filtered to remove the hydroxylamine, and the filtrate is washed with 10 w/v % ascorbic acid (3×33 mL) and distilled water (2×50 mL). The organic phase is dried over anhydrous sodium sulfate and the volatiles are removed in vacuo. The residue is recrystallized from acetonitrile to give 4.03 g (51% yield) of a white solid melting at 163–164.5° C.

$^1$Hnmr (CDCL$_3$)(499.8493 MHz) δ 1.27 (s, 6H), 1.29 (s, 6H), 1.37 (dd, 2H), 1.83 (dd, 2H), 1.96 (s, 3H), 2.37 (s, 3H), 4.17 (m, 1H), 4.70 (s, 2H), 5.18 (d, NH, 1H), 7.11 (d, 1H), 7.15 (d, 1H), 7.16 (d, 1H), 7.24 (t, 1H).

Analysis:
Calc'd for C$_{19}$H$_{30}$N$_2$O$_2$: C, 71.66; H, 9.50; N, 8.80.
Found: C, 71.39; H, 9.26; N, 8.99.

EXAMPLE 6

1-Benzyloxy-4-hydroxy-2,2,6,6-tetramethylpiperidine

A mixture of 2.58 g (0.015 mol) of 1-oxyl-4-hydroxy-2,2,6,6-tetramethylpiperidine and 27.64 g (0.30 mol) of toluene under a nitrogen atmosphere is heated in a pressure vessel for 53 hours. The reaction mixture is diluted with diethyl ether and the resultant mixture is washed with 10 w/v % ascorbic acid (1×50 mL) and distilled water (2×50 mL). The organic phase is dried over anhydrous sodium sulfate and the volatiles are removed in vacuo. The residue is recrystallized from heptane to give 0.59 g (30% yield) of a white solid melting at 86–87° C.

IR (1% solution in methylene chloride) v 3595 cm$^{-1}$ (OH).

$^1$Hnmr (CDCL$_3$)(499.8493 MHz) δ 1.12 (s, 6H), 1.23 (s, 6H), 1.44 (dd, 2H), 1.59 (m, 2H), 3.65 (tt, 1H), 4.82 (s, 2H), 7.09 (t, 1H), 7.16 (t, 2H), 7.32 (d, 2H).

Analysis:
Calc'd for C$_{16}$H$_{25}$NO$_2$: C, 72.97; H, 9.57; N, 5.32.
Found: C, 73.18; H, 9.63; N, 4.99.

EXAMPLE 7

1-(1-Phenylethyl)oxy-4-hydroxy-2,2,6,6-tetramethylpiperidine

A mixture of 17.23 g (0.10 mol) of 1-oxyl-4-hydroxy-2,2,6,6-tetramethylpiperidine and 106.17 g (1.0 mol) of ethylbenzene under a nitrogen atmosphere is heated at 133° C. for 26 hours. The volatiles are removed in vacuo and the residue is triturated with diethyl ether. The precipitate of 1,4-dihydroxy-2,2,6,6-tetramethylpiperidine is collected by filtration to give 12.57 g of an off-white solid.

$^1$Hnmr (dimethyl sulfoxide-d$_6$)(499.8493 MHz) δ 1.02 (s, 6H), 1.05 (s, 6H), 1.24 (dd, 2H), 1.69 (dd, 2H), 3.32 (s, 1H), 3.73 (m, 1H), 4.36 (d, 1H).

The filtrate from the above filtration is washed with 10 w/v % ascorbic acid (3×33 mL) and distilled water (2×50 mL). The organic phase is dried over anhydrous sodium sulfate and the volatiles are removed in vacuo. The residue is recrystallized from acetonitrile to give 0.82 g (6% yield) of a white solid melting at 97–98° C.

$^1$Hnmr (CDCL$_3$)(499.8493 MHz) δ 0.69 (s, 3H), 1.09 (s, 3H), 1.16 (d, OH, 1H), 1.23 (s, 3H), 1.35 (s, 3H), 1.39 (dd, 1H), 1.49 (dd, 1H), 1.50 (d, 3H), 1.72 (ddd, 1H) 1.85 (dd, 1H), 3.95 (m, 1H), 4.79 (q, 1H), 7.25 (m, 1H), 7.20–7.33 (overlapping m, 4H).

Analysis:
Calc'd for C$_{17}$H$_{27}$NO$_2$: C, 73.61; H, 9.81; N, 5.05.
Found: C, 73.42; H, 9.68; N, 4.93.

EXAMPLE 8

Reoxidation of 1,4-Dihydroxy-2,2,6,6-tetramethylpiperidine to 1-Oxyl-4-hydroxy-2,2,6,6-tetramethylpiperidine To a solution of 2.0 g of 1,4-dihydroxy-2,2,6,6-tetramethylpiperidine in 25 mL of water at 80° C. is added dropwise two (2) equivalents of 30% hydrogen peroxide. The conversion of 1,4-dihydroxy-2,2,6,6-tetramethylpiperidine to 1-oxyl-4-hydroxy-2,2,6,6-tetramethylpiperidine as determined by both TLC and GLC (Varian Model 3400 Gas Chromatograph; J&W Scientific DB 1 Column; 15 m) is 100%.

EXAMPLE 9

1-(4-Methylbenzyl)oxy-4-hydroxy-2,2,6,6-tetramethylpiperidine

A mixture of 8.60 g (0.1 mol) of 1-oxyl-4-hydroxy-2,2,6,6-tetramethylpiperidine and 53.09 g (0.5 mol) of p-xylene in 61 mL of chlorobenzene under a nitrogen atmosphere is heated at 140° C. for 56 hours. The reaction mixture is filtered to remove 1,4-dihydroxy-2,2,6,6-tetramethylpiperidine, and the filtrate is washed with 10 w/v % ascorbic acid (3×30 mL) and distilled water (2×50 mL). The organic phase is dried over anhydrous sodium sulfate and the volatiles are removed in vacuo. The residue is recrystallized from heptane to give 3.33 g (48% yield) of the title compound as a white solid melting at 92.5–93° C.

EXAMPLE 10

1-(2-Phenylallyloxy)-4-benzoyloxy-2,2,6,6-tetramethylpiperidine

A mixture of 1.0 g (3.6 mmol) of 1-oxyl-4-benzoyloxy-2,2,6,6-tetramethylpiperidine and 10 g (85 mmol) of α-methylstyrene under a nitrogen atmosphere is heated at 120° C. for 36 hours. The reaction mixture is concentrated in vacuo and the title compound is isolated as a pale yellow oil after column chromatography.

EXAMPLE 11

1-(3-Phenylallyloxy)-4-benzoyloxy-2,2,6,6-tetramethylpiperidine

A mixture of 1.0 g (3.6 mmol) of 1-oxyl-4-benzoyloxy-2,2,6,6-tetramethylpiperidine and 10 g (85 mmol) of β-methylstyrene under a nitrogen atmosphere is heated at 120° C. for 36 hours. The reaction mixture is concentrated in vacuo and the title compound is isolated after column chromatograph as a white solid, melting at 115–116° C.

EXAMPLE 12

1-Diphenylmethoxy-4-benzoyloxy-2,2,6,6-tetramethylpiperidine

A mixture of 1.0 g (3.6 mmol) of 1-oxyl-4-benzoyloxy-2,2,6,6-tetramethylpiperidine and 10 g (60 mmol) of diphenylmethane under a nitrogen atmosphere is heated at 100° C. for 24 hours. The reaction mixture is concentrated in vacuo and the title compound is isolated after column chromatograph as a white solid, melting at 135–136° C.

EXAMPLE 13

1-(Cyclooct-2-enyloxy)-2,2,6,6-tetramethyl-4-hydroxypiperidine

A mixture of 15.0 g (0.09 mol) of 1-oxyl-4-hydroxy-2,2,6,6-tetramethylpiperidine and 126.6 g (1.15 mol) of cyclooctene is heated under a nitrogen atmosphere at 87–88° C. for 40 hours. The reaction mixture is filtered to remove 1,4-dihydroxy-2,2,6,6-tetramethylpiperidine, and the filtrate is washed with 5% ascorbic acid (2×50 mL) and distilled water (2×50 mL). The organic phase is dried over anhydrous magnesium sulfate and the volatiles removed in vacuo. The residue is crystallized from heptane to give 4.40 g (36% yield) of the title compound as a white solid.

$^1$Hnmr (CDCL$_3$)(500 MHz) δ 1.14 (s, 3H), 1.16 (s, 3H), 1.21 (s, 3H), 1.26 (s, 3H), 1.27–2.20 (m, 14H), 3.95 (m, 1H), 4.64 (m, 1H), 5.54–5.64 (m, 2H).

Analysis:

Calc'd for C$_{17}$H$_{31}$NO$_2$: C, 72.55; H, 11.10; N, 4.98.
Found: C, 72.69; H, 11.13; N, 4.73.

EXAMPLE 14

1-(Cyclohex-2-enyloxy)-2,2,6,6-tetramethylpiperidin-4-one

A mixture of 25.0 g (0.15 mol) of 1-oxyl-4-oxo-2,2,6,6-tetramethylpiperidine and 162.2 g (1.97 mol) of cyclohexene is heated under a nitrogen atmosphere at 85–86° C. for 56 hours. The reaction mixture is filtered to remove the hydroxylamine, and the solvent is removed in vacuo. The residue is dissolved in heptane and washed with 5% ascorbic acid (2×50 mL) and distilled water (2×50 mL). The organic phase is dried over anhydrous magnesium sulfate and the volatiles removed in vacuo. The residue is eluted through a silica gel column with heptane/ethyl acetate (9/1) to give 3.9 g (21% yield) of the title compound as a yellow oil.

$^1$Hnmr (CDCL$_3$)(500 MHz) δ 1.10–2.12 (m, 18H), 2.24 (d, 2H), 2.57 (d, 2H), 4.34 (m, 1H), 5.85 (m, 1H), 5.98 (m, 1H).

Analysis:

Calc'd for C$_{15}$H$_{25}$NO$_2$: C, 71.67; H, 10.02; N, 5.57.
Found: C, 71.79; H, 10.16; N, 5.60.

EXAMPLE 15

1-(Cycloocta-2,6-dienyloxy)-2,2,6,6-tetramethyl-4-hydroxypiperidine

A mixture of 29.4 g (0.17 mol) of 1-oxyl-4-hydroxy-2,2,6,6-tetramethylpiperidine and 148.0 g (1.37 mol) of 1,5-cyclooctadiene is heated under a nitrogen atmosphere at 100° C. for 24 hours. The reaction mixture is filtered to remove 1,4-dihydroxy-2,2,6,6-tetramethylpiperidine, and the filtrate is diluted with heptane (250 mL). The organic phase is washed with 5% ascorbic acid (2×50 mL) and distilled water (2×50 mL). The organic phase is dried over anhydrous magnesium sulfate and the volatiles removed in vacuo. The residue is chromatographed to give 8.1 g (33% yield) of the title compound as a white solid.

$^1$Hnmr (CDCL$_3$)(500 MHz) δ 1.10–1.28 (m, 12H), 1.47 (t, 2H), 1.82 (d, 2H), 2.06–2.26 (m, 2H), 2.29 (m, 1H), 2.40 (m, 1H), 2.86 (d, 1H), 3.96 (tt, 1H), 5.01 (m, 1H), 5.40–5.70 (m, 4H).

EXAMPLE 16

1-Oct-2-enyloxy-2,2,6,6-tetramethyl-4-hydroxypiperidine

A mixture of 20.0 g (0.12 mol) of 1-oxyl-4-hydroxy-2,2,6,6-tetramethylpiperidine and 164.0 g (1.04 mol) of 1-octene is heated under a nitrogen atmosphere at 100° C. for 24 hours, and then for an additional 24 hours at 115° C. The reaction mixture is filtered to remove 1,4-dihydroxy-2,2,6,6-tetramethylpiperidine, and the filtrate is washed with 10% (w/v) ascorbic acid (2×50 mL) and distilled water (2×50 mL). The organic phase is dried over anhydrous magnesium sulfate and the volatiles removed in vacuo. The residue is chromatographed to give 14.4 g (83% yield) of the title compound as an amber oil.

$^1$Hnmr (CDCL$_3$)(500 MHz) δ 0.9 (t, 3H), 1.10–1.36 (m, 16H), 1.39 (m, 2H), 1.45 (t, 2H), 1.82 (d, 2H), 2.04 (q, 2H), 3.96 (m, 1H), 4.20–4.33 (broad d, 2H), 5.50 (m, 1H), 5.68 (m, 4H).

EXAMPLE 17

Recycling of Hydroxylamine to N-oxyl

In Examples 1–7 and 9–16, along with the desired N—OR compound formed, an equivalent amount of the corresponding N—OH compound is also present. The hydroxylamines are insoluble in the solvents such as toluene or xylene and can be easily separated from the reaction mixtures by simple filtration as indicated in the various working Examples. After separation from the reaction mixture and from the desired N—OR compound by filtration, the corresponding N—OH compound is oxidized using hydrogen peroxide back to the correspond N-oxyl compound needed as an intermediate for Step 2.

What is claimed is:

1. A process, involving two steps for the preparation of a selected N—OR derivative of the 2,2,6,6-tetraalkylpiperidines with a third step involving the recycling of the N—OH obtained concomitantly with the desired N—OR compound back to the corresponding N-oxyl starting material for the second step, which comprises in Step 1, preparing an N-oxyl compound by oxidation with hydrogen peroxide

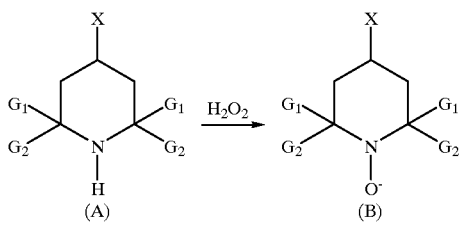

and, in Step 2, reacting two equivalents of N-oxyl with one allylic, benzylic or activated methine compound (R—H) to form one equivalent of N—OH and one equivalent of N—OR compound

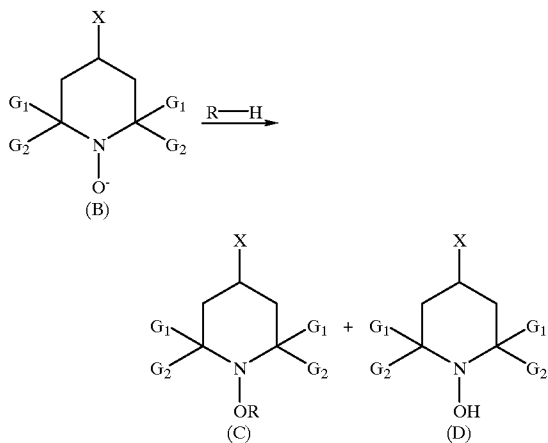

separating the N—OH and N—OR compounds, and, in Step 3, recycling the N—OH compound formed in Step 2 back to the N-oxyl compound needed as intermediate for Step 2

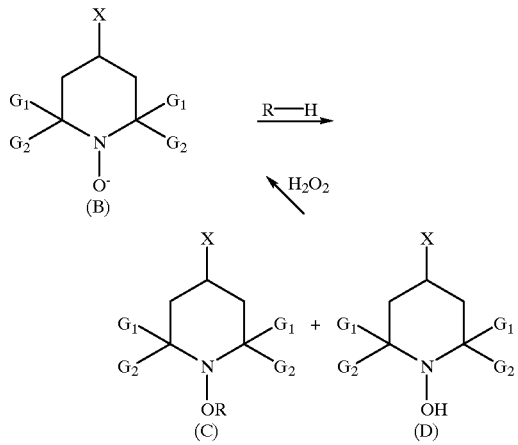

where in the formulas A, B, C and D,

G$_1$ and G$_2$ are independently alkyl of 1 to 4 carbon atoms, or G$_1$ and G$_2$ together are pentamethylene;

X is hydrogen, hydroxyl, oxo, —NH—CO—E, —O—CO—E or —NH—CO—NH—E, where E is alkyl of 1 to 18 carbon atoms or said alkyl substituted by hydroxyl, or E is aryl of 6 to 10 carbon atoms; and R is an alkenyl of 3 to 20 carbon atoms; Y—CH—Z where Y and Z are independently, hydrogen, alkyl of 1 to 18 carbon atoms, aryl of 6 to 10 carbon atoms or said aryl substituted by one to four alkyl groups of 1 to 4 carbon atoms, provided that at least one of Y and Z is aryl and where is Y is aryl, then Z can be part of a fused ring system having methylene groups.

2. A process according to claim 1 wherein G$_1$ and G$_2$ are each methyl.

3. A process according to claim 1 where in Step 2, the compound R—H is cyclohexene, 1,5-cyclooctadiene, cyclooctene, 1-octene, allylbenzene, α-methylstyrene, β-methylstyrene 1,2,3,4-tetrahydronaphthalene, toluene, o-xylene, m-xylene, p-xylene, diphenylmethane, ethylbenzene, mesitylene or durene.

4. A process according to claim 3 wherein the compound R—H is cyclohexene, 1,5-cyclooctadiene, cyclooctene, 1-octene, α-methylstyrene, β-methylstyrene, toluene, m-xylene, p-xylene, diphenylmethane or ethylbenzene.

5. A process according to claim 1 where in Step 2, the oxyl compound of formula B is 1-oxyl-4-hydroxy-2,2,6,6-tetramethylpiperidine, 1-oxyl-4-acetamido-2,2,6,6-tetramethylpiperidine, 1-oxyl-4-oxo-2,2,6,6-tetramethylpiperidine or 1-oxyl-4-benzoyloxy-2,2,6,6-tetramethylpiperidine.

6. A process according to claim 1 where in Step 1 and in Step 3, the concentration of aqueous hydrogen peroxide is 30% by weight or higher.

7. A process according to claim 6 wherein the concentration of aqueous hydrogen peroxide is 30%, 50% or 70% by weight.

8. A process according to claim 1 wherein Step 2 is carried out in the absence of solvent or in the presence of an inert solvent such a chlorobenzene.

9. A process according to claim 1 wherein Step 2 is carried out at a temperature of 50 to 140° C. at atmospheric pressure.

10. A process according to claim 1 wherein Step 2 is carried out at a temperature of 50 to 140° C. in a pressure vessel.

11. A process, for the preparation of a selected N—OR derivative of the 2,2,6,6-tetraalkylpiperidines followed by a subsequent step involving the recycling of the N—OH obtained concomitantly with the desired N—OR compound back to the corresponding N-oxyl starting material for the initial step, which comprises reacting two equivalents of N-oxyl with one allylic, benzylic or activated methine compound (R—H) to form one equivalent of N—OH and one equivalent of N—OR compound

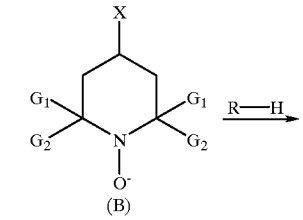

-continued

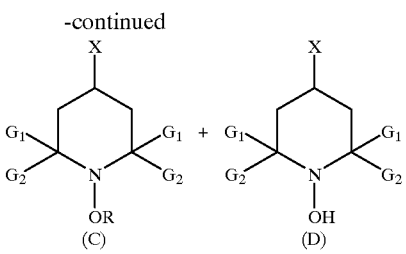

separating the N—OH and N—OR compounds, and,
recycling the N—OH compound formed back to the N-oxyl compound needed as intermediate for the initial reaction

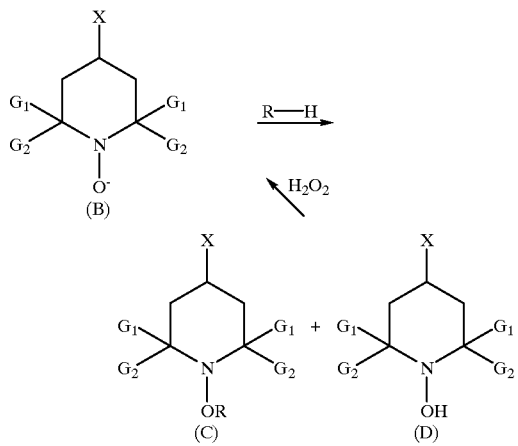

where in the formulas B, C and D, $G_1$ and G2 are independently alkyl of 1 to 4 carbon atoms, or $G_1$ and $G_2$ together are pentamethylene;

X is hydrogen, hydroxyl, oxo, —NH—CO—E, —O—CO—E or —NH—CO—NH—E, where E is alkyl of 1 to 18 carbon atoms, said alkyl substituted by hydroxyl or E is aryl of 6 to 10 carbon atoms; and R is an alkenyl of 3 to 20 carbon atoms; Y—CH—Z where Y and Z are independently, hydrogen, alkyl of 1 to 18 carbon atoms, aryl of 6 to 10 carbon atoms or said aryl substituted by one to four alkyl groups of 1 to 4 carbon atoms, provided that at least one of Y and Z is aryl and where is Y is aryl, then Z can be part of a fused ring system having methylene groups.

12. A process according to claim 11 wherein $G_1$ and $G_2$ are each methyl.

13. A process according to claim 11 where the compound R—H is cyclohexene, 1,5-cyclooctadiene, cyclooctene, 1-octene, allylbenzene, α-methylstyrene, β-methylstyrene 1,2,3,4-tetrahydronaphthalene, toluene, o-xylene, m-xylene, p-xylene, diphenylmethane, ethylbenzene, mesitylene or durene.

14. A process according to claim 13 wherein the compound R—H is cyclohexene, 1,5-cyclooctadiene, cyclooctene, 1-octene, α-methylstyrene, β-methylstyrene, toluene, m-xylene, p-xylene, diphenylmethane or ethylbenzene.

15. A process according to claim 11 where the oxyl compound of formula B is 1-oxyl-4-hydroxy-2,2,6,6-tetramethylpiperidine, 1-oxyl-4-acetamido-2,2,6,6-tetramethylpiperidine, 1-oxyl-4-oxo-2,2,6,6-tetramethylpiperidine or 1-oxyl-4-benzoyloxy-2,2,6,6-tetramethylpiperidine.

16. A process according to claim 11 where in the recycle step, the concentration of aqueous hydrogen peroxide is 30% by weight or higher.

17. A process according to claim 16 wherein the concentration of aqueous hydrogen peroxide is 30%, 50% or 70% by weight.

18. A process according to claim 11 wherein the reaction is carried out in the absence of solvent or in the presence of an inert solvent such a chlorobenzene.

19. A process according to claim 11 wherein the reaction is carried out at a temperature of 50 to 140° C. at atmospheric pressure.

20. A process according to claim 11 wherein the reaction is carried out at a temperature of 50 to 140° C. in a pressure vessel.

21. A process, for the preparation of a selected N—OR derivative of the 2,2,6,6-tetraalkylpiperidines, which comprises reacting two equivalents of N-oxyl with one allylic, benzylic or activated methine compound (R—H) to form one equivalent of N—OH and one equivalent of N—OR compound

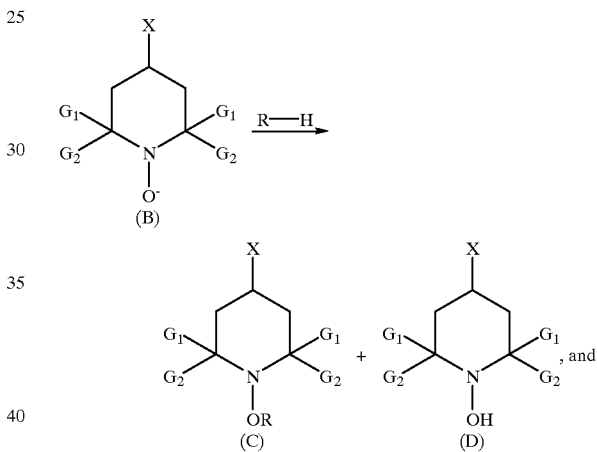

separating the N—OH and N—OR compounds,
where in the formulas B, C and D, $G_1$ and $G_2$ are independently alkyl of 1 to 4 carbon atoms, or $G_1$ and $G_2$ together are pentamethylene;

X is hydrogen, hydroxyl, oxo, —NH—CO—E, —O—CO—E or —NH—CO—NH—E, where E is alkyl of 1 to 18 carbon atoms, said alkyl substituted by hydroxyl or E is aryl of 6 to 10 carbon atoms; and R is an alkenyl of 3 to 20 carbon atoms; Y—CH—Z where Y and Z are independently, hydrogen, alkyl of 1 to 18 carbon atoms, aryl of 6 to 10 carbon atoms or said aryl substituted by one to four alkyl groups of 1 to 4 carbon atoms, provided that at least one of Y and Z is aryl and where is Y is aryl, then Z can be part of a fused ring system having methylene groups.

22. A process according to claim 21 wherein $G_1$ and $G_2$ are each methyl.

23. A process according to claim 21 where the compound R—H is cyclohexene, 1,5-cyclooctadiene, cyclooctene, 1-octene, allylbenzene, α-methylstyrene, β-methylstyrene 1,2,3,4-tetrahydronaphthalene, toluene, o-xylene, m-xylene, p-xylene, diphenylmethane, ethylbenzene, mesitylene or durene.

24. A process according to claim 23 wherein the compound R—H is cyclohexene, 1,5-cyclooctadiene, cyclooctene, 1-octene, α-methylstyrene, β-methylstyrene, toluene, m-xylene, p-xylene, diphenylmethane or ethylbenzene.

25. A process according to claim 21 where the oxyl compound of formula B is 1-oxyl-4-hydroxy-2,2,6,6-tetramethylpiperidine, 1-oxyl-4-acetamido-2,2,6,6-tetramethylpiperidine, 1-oxyl-4-oxo-2,2,6,6-tetramethylpiperidine or 1-oxyl-4-benzoyloxy-2,2,6,6tetramethylpiperidine.

26. A process according to claim 21 wherein the reaction is carried out in the absence of solvent or in the presence of an inert solvent such a chlorobenzene.

27. A process according to claim 21 wherein the reaction is carried out at a temperature of 50 to 140° C. at atmospheric pressure.

28. A process according to claim 21 wherein the reaction is carried out at a temperature of 50 to 140° C. in a pressure vessel.

* * * * *